US011499957B1

United States Patent
Wang et al.

(10) Patent No.: US 11,499,957 B1
(45) Date of Patent: Nov. 15, 2022

(54) EVALUATION METHOD FOR RESIDUAL HYDROCARBON OF POST- TO OVER-MATURE MARINE SOURCE ROCKS

(71) Applicant: INSTITUTE OF GEOLOGY AND GEOPHYSICS, CHINESE ACADEMY OF SCIENCES, Beijing (CN)

(72) Inventors: Wenyang Wang, Beijing (CN); Yaping Wang, Beijing (CN); Xiongqi Pang, Beijing (CN); Zhangxing Chen, Beijing (CN); Wang Zhang, Beijing (CN); Rixiang Zhu, Beijing (CN)

(73) Assignee: INSTITUTE OF GEOLOGY AND GEOPHYSICS, CHINESE ACADEMY OF SCIENCES, Beijing (CN)

(*) Notice: Subject to any disclaimer, the term of this patent is extended or adjusted under 35 U.S.C. 154(b) by 0 days.

(21) Appl. No.: 17/531,814

(22) Filed: Nov. 22, 2021

(30) Foreign Application Priority Data

Aug. 20, 2021 (CN) .......................... 20211096067.2

(51) Int. Cl.
*G01K 13/00* (2021.01)
*G01N 33/24* (2006.01)
(Continued)

(52) U.S. Cl.
CPC .......... *G01N 33/241* (2013.01); *G01N 25/20* (2013.01); *G06F 30/28* (2020.01); *G01K 13/00* (2013.01)

(58) Field of Classification Search
CPC ...... G01N 33/241; G01N 33/24; G01N 31/12; G01N 1/4022; G01N 2001/4033;
(Continued)

(56) References Cited

U.S. PATENT DOCUMENTS

2008/0059140 A1 3/2008 Salmon et al.
2015/0127313 A1 5/2015 Lawson et al.
(Continued)

FOREIGN PATENT DOCUMENTS

AU 2014259680 A1 * 12/2015 ......... G01N 21/3563
CN 103926389 A 7/2014
(Continued)

OTHER PUBLICATIONS

"Kinetics of hydrocarbon generation as a function of the molecular structure of kerogen as revealed by pyrolysis-gas chromatography". Erik W. Tegelaar et al. (Year: 2003).*
(Continued)

*Primary Examiner* — Gail Kaplan Verbitsky
(74) *Attorney, Agent, or Firm* — Bayramoglu Law Offices LLC

(57) ABSTRACT

An evaluation method for residual hydrocarbon of post- to over-mature marine source rocks includes the following steps: establishing a hydrocarbon generation potential evolution profile and a hydrogen index evolution profile of post- to over-mature source rocks; determining a critical condition for hydrocarbon expulsion of the source rocks, and inverting original hydrocarbon generation potential of the source rocks; inverting a critical condition for hydrocarbon generation of the source rocks; establishing a hydrocarbon generation, expulsion and retention model for the source rocks; determining a hydrocarbon generation rate, a hydrocarbon expulsion rate and a hydrocarbon retention rate of the source rocks; and calculating a hydrocarbon retention intensity and residual hydrocarbon of the source rocks. The evaluation method establishes an evaluation model for residual hydrocarbon of post- to over-mature source rocks without relying on immature to sub-mature samples.

2 Claims, 4 Drawing Sheets

(51) Int. Cl.
  *G06F 30/28* (2020.01)
  *G01N 25/20* (2006.01)
(58) Field of Classification Search
  CPC ....... G01N 2030/123; G01N 2030/125; G01N 30/12; G01N 30/7206; G01N 30/8679; G01N 23/2251; G01N 25/18; G01N 33/2823; G01N 2021/3595; G01N 21/3563; G01N 2223/0563; G01N 2223/071; G01N 2223/079; G01N 2223/616; G01N 23/20091; G01N 3/062; G01N 3/066; G01N 1/28; G01N 1/34; G01N 1/44; G01N 15/08; G01N 15/088; G01N 23/20075; G01N 25/00; B01J 6/008
  See application file for complete search history.

(56) References Cited

U.S. PATENT DOCUMENTS

2018/0134964 A1* 5/2018 Inan ............... G01N 33/241
2020/0231878 A1* 7/2020 Inan ............... G01N 33/241

FOREIGN PATENT DOCUMENTS

| CN | 105223340 A | | 1/2016 | |
|---|---|---|---|---|
| CN | 105403585 A | * | 3/2016 | |
| CN | 106056459 A | | 10/2016 | |
| CN | 107966545 A1 | * | 4/2018 | |
| CN | 110632274 A | * | 12/2019 | |
| CN | 11662962 A1 | * | 1/2020 | |
| CN | 114460122 A | * | 5/2022 | |
| WO | WO-2016081669 A1 | * | 5/2016 | ............... G01V 3/30 |

OTHER PUBLICATIONS

"Assessing thermal maturity beyond the reaches of vitrinite reflectance and Rock-Eval pyrolysis: A case study from the Silurian Qusaiba formation". Stephen Cheshire et al. (Year: 2017).*
Li Zhong-Bo, Hydrocarbon generation potential evaluation of high and over matured source rocks in Lishu fault depression, Songliao Basin, Global Geology, 2020, pp. 617-625, vol. 39, No. 3.
Chen Junqing, Hydrocarbon expulsion characteristics and effectiveness evaluation of low abundance source rock of Ordovician, platform of Tarim Basin, 2018, pp. 1-131.

* cited by examiner

EVALUATION METHOD FOR RESIDUAL HYDROCARBON OF POST- TO OVER-MATURE MARINE SOURCE ROCKS

CROSS REFERENCE TO THE RELATED APPLICATIONS

This application is based upon and claims priority to Chinese Patent Application No. 202110960671.2, filed on Aug. 20, 2021, the entire contents of which are incorporated herein by reference.

TECHNICAL FIELD

The present disclosure belongs to the technical field of oil and gas exploitation, and in particular relates to an evaluation method for residual hydrocarbon of post- to over-mature marine source rocks.

BACKGROUND

Huge shale oil and gas resources are contained in the source rock strata. Residual hydrocarbon determines the potential of shale oil and gas resources, and the evaluation of residual hydrocarbon is of great significance for the evaluation of shale oil and gas resources and the selection of excellent exploration targets. However, the geochemistry community has long faced a difficult problem, that is, how to establish an evaluation model for residual hydrocarbon of post- to over-mature marine source rocks, and to calculate residual hydrocarbon of post- to over-mature marine source rocks. The fundamental reason for this long-standing problem lies in that the natural marine source rocks generally have a high maturity and there are few immature mature source rocks and sub-mature source rocks, which makes it hard to reconstruct a complete hydrocarbon generation, expulsion and retention evolution process of source rocks.

The most important parameters involved in the evaluation of residual hydrocarbon in the source rocks include a critical condition for hydrocarbon generation and the determination of residual hydrocarbon potential that changes with the degree of thermal evolution. In the prior art, in order to solve the problem of evaluating the residual hydrocarbon in the post- to over-mature marine source rocks, the following methods were used. 1) The critical condition for hydrocarbon generation was determined empirically, for example, the degree of thermal evolution $R_o$ (i.e. vitrinite reflectance) might be taken as 0.4%, 0.5% or 0.6%, etc. 2) Immature and sub-mature marine source rocks from relatively newer shallow strata in the same basin or from strata of the same age in different basins were used to make up for the lack of immature and sub-mature samples in the study strata, and residual hydrocarbon was calculated by using the hydrocarbon generation potential method.

These methods have the following shortcomings. First, different types of source rocks have different critical conditions for hydrocarbon expulsion, and have the definitions of critical conditions for hydrocarbon generation are quite different in different scholars' views, which are subjective, unscientific, and cannot be widely used. Second, it is hard to find alternative immature and sub-mature source rock samples. No immature and sub-mature source rocks have been found in the Lower Paleozoic marine strata in China, and there are generally few immature and sub-mature source rocks in the ancient marine strata. In addition, it is problematic to use the immature or sub-mature marine source rocks from relatively newer shallow strata in the same or different basins for making up for the lack of sub-mature source rocks because there are great differences in depositional environment, organic facies, organic matter types and organic matter enrichment conditions, which play an important role in the hydrocarbon generation, expulsion and retention evolution of source rocks. If the residual hydrocarbon characteristics of the source rocks are not well understood, it is hard to scientifically predict the potential of shale oil and gas resources according to the genesis, which finally affects the selection and evaluation of shale oil and gas exploration targets.

SUMMARY

The present disclosure provides an evaluation method for residual hydrocarbon of post- to over-mature marine source rocks. The present disclosure aims to solve the technical problem that the existing evaluation method for residual hydrocarbon of post- to over-mature source rocks has low accuracy and relies on immature to sub-mature samples. The method includes the following steps: S100: establishing a hydrocarbon generation potential evolution profile and a hydrogen index evolution profile of post- to over-mature source rocks; S200: determining a critical condition for hydrocarbon expulsion of the source rocks, and inverting original hydrocarbon generation potential of the source rocks; S300: inverting a critical condition for hydrocarbon generation of the source rocks; S400: establishing a hydrocarbon generation, expulsion and retention model for the source rocks; S500: determining a hydrocarbon generation rate, a hydrocarbon expulsion rate and a hydrocarbon retention rate of the source rocks; and S600: calculating a hydrocarbon retention intensity and residual hydrocarbon of the source rocks.

In some preferred examples, step S100 may include: obtaining a hydrocarbon generation potential index, a hydrogen index and an equivalent vitrinite reflectance through a pyrolysis experiment of the source rocks; and establishing a hydrocarbon generation potential evolution profile and a hydrogen index evolution profile of post- to over-mature source rocks for marine strata lacking vitrinite based on the hydrocarbon generation potential index, the hydrogen index and the equivalent vitrinite reflectance, where the hydrocarbon generation potential evolution profile of the source rocks is a diagram showing a relationship between the hydrocarbon generation potential index and the equivalent vitrinite reflectance; and the hydrogen index evolution profile of the source rocks is a diagram showing a relationship between the hydrogen index and the equivalent vitrinite reflectance;

the hydrocarbon generation potential index is $100 \times (S_1 + S_2)/TOC$, where $S_1$, $S_2$ are hydrocarbon yields per unit mass of source rock samples heated to 300° C. and 300-600° C. respectively, mg·HC/g; TOC is total organic carbon (TOC) per unit mass of the source rocks, mg/g;

the hydrogen index is $100 \times S_2/TOC$; and the equivalent vitrinite reflectance is $R_o$, $R_0 = 0.0078 T_{max} - 1.3654$, where $T_{max}$ is a maximum peak pyrolysis temperature in the pyrolysis experiment of the source rocks.

In some preferred examples, the determining a critical condition for hydrocarbon expulsion may include: obtaining a homogenization temperature distribution map of fluid inclusions according to an inclusion experiment; determining a main peak value of a homogenization temperature for a first phase of the fluid inclusions based on the homogenization temperature distribution map of the fluid inclusions; and obtaining a corresponding minimum $R_{min}$ of an isotherm at the main peak value of the homogenization temperature of the first phase of the inclusions according to a depositional burial history and a thermal evolution history of a typical well, which is $R_{oe}$, meaning a critical maturity for hydrocarbon expulsion corresponding to the critical condition for hydrocarbon expulsion.

In some preferred examples, the inverting original hydrocarbon generation potential of the source rocks may include: obtaining a hydrocarbon generation potential index envelope $I_g$ according to the hydrocarbon generation potential evolution profile of the source rocks, $$I_g = \frac{a}{1+e^{-b(R_o-c)}} + d,$$

where a, b, c and d are constants; and obtaining an original hydrocarbon generation potential $I_{og}$ of the source rocks based on the hydrocarbon generation potential index envelope and the critical maturity for hydrocarbon expulsion, $$I_{og} = \frac{a}{1+e^{-b(R_{oe}-c)}} + d.$$

In some preferred examples, the inverting a critical condition for hydrocarbon generation of the source rocks may include: obtaining a hydrogen index envelope based on the hydrogen index evolution profile of the source rocks HI, $$HI = \frac{e}{1+e^{-f(R_o-g)}} + h,$$

where e, f, g and h are constants; and obtaining a critical condition $R_{og}$ for hydrocarbon generation of the source rocks based on the hydrogen index envelope and the original hydrocarbon generation potential of the source rocks, where $R_{og}$ is an equivalent vitrinite reflectance corresponding to an intersection of the hydrogen index envelope and the original hydrocarbon generation potential of the source rocks.

In some preferred examples, the establishing a hydrocarbon generation, expulsion and retention model for the source rocks may include: establishing a hydrocarbon generation, expulsion and retention model for the source rocks by means of matrix laboratory (MATLAB) based on the hydrocarbon generation potential evolution profile, the hydrogen index evolution profile, the critical condition for hydrocarbon expulsion, the original hydrocarbon generation potential and the critical condition for hydrocarbon generation of the source rocks; and marking $R_{og}$, $R_{oe}$, HI, $I_g$ and $I_{og}$ in the model.

In some preferred examples, step S500 may include: calculating a hydrocarbon generation rate, a hydrocarbon expulsion rate and a hydrocarbon retention rate of the source rocks based on the hydrocarbon generation, expulsion and retention model for the source rocks, where the hydrocarbon generation rate of the source rocks is $q_g$, $q_g = I_{og} - HI$;

the hydrocarbon expulsion rate of the source rocks is $q_e$, $q_e = I_{og} - I_g$; and the hydrocarbon retention rate of the source rocks is $q_r$, $q_r = q_g - q_e$.

In some preferred examples, the calculating a hydrocarbon retention intensity of the source rocks may include: obtaining a hydrocarbon retention intensity $I_r$ of the source rocks in different thermal evolution stages by an integral of the hydrocarbon retention rate, abundance of organic matter and a thickness and density of the source rocks corresponding to the different thermal evolution stages, where $$I_r = \int_{R_o^i}^{R_o} 10^{-3} * q_r * H * \rho * TOC_O * d(R_o); \text{ and}$$

H is the thickness of the source rocks; ρ is the density of the source rocks; A is a distribution area of the source rocks; and $TOC_O$ is original TOC of the source rock.

In some preferred examples, $TOC_o = TOC*k$; and $$k = \left(1 - 0.83 * \frac{I_g}{1000}\right) \Big/ \left(1 - 0.83 * \frac{I_{og}}{1000}\right).$$

In some preferred examples, the total residual hydrocarbon $Q_r$ in each geological period may be obtained based on the hydrocarbon retention intensity, where $$Q_r = \int_{R_o^i}^{R_o} 10^{-13} * q_r * H * A * \rho * TOC_O * d(R_o).$$

1) The present disclosure establishes a residual hydrocarbon model for post- to over-mature source rocks without relying on immature to sub-mature samples, which can be used to study the residual hydrocarbon characteristics of post- to over-mature source rocks.

2) The present disclosure forms a process for evaluating the residual hydrocarbon of post- to over-mature marine source rocks, which can scientifically calculate the residual hydrocarbon of marine source rocks in strata lacking immature to sub-mature samples.

Therefore, the present disclosure provides a scientific basis for the evaluation of the potential of deep oil and gas resources. The present disclosure provides a scientific basis for the evaluation of shale oil and gas resources, and provides strong theoretical guidance and technical support for the selection and evaluation of shale oil and gas exploration targets.

BRIEF DESCRIPTION OF THE DRAWINGS

Other features, objectives and advantages of the present application will become more apparent upon reading the detailed description of the non-restrictive examples with reference to the following drawings.

DETAILED DESCRIPTION OF THE EMBODIMENTS

Figure 1:
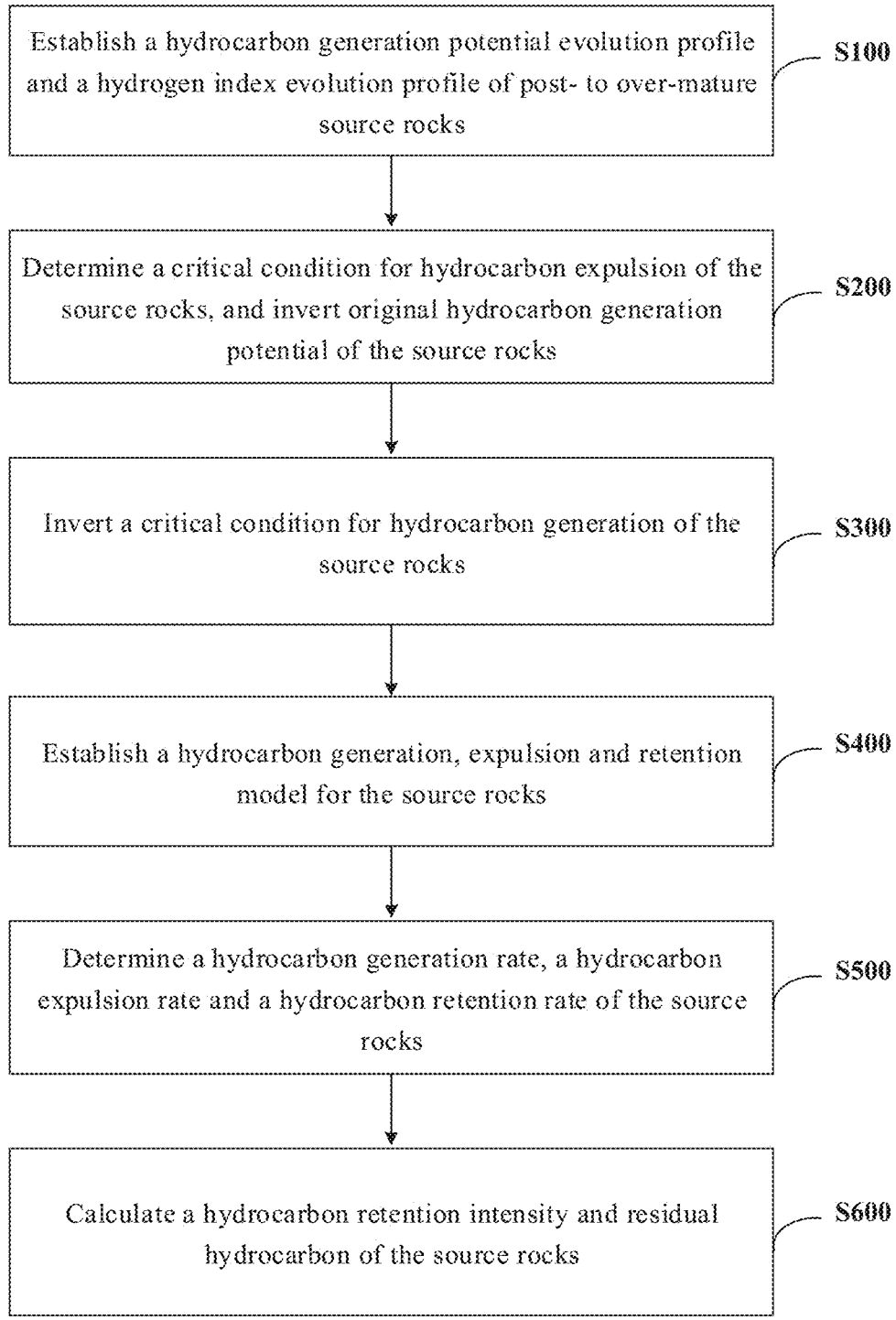
FIG. 1 is a flowchart of an example of the present disclosure.
Figure 2A:
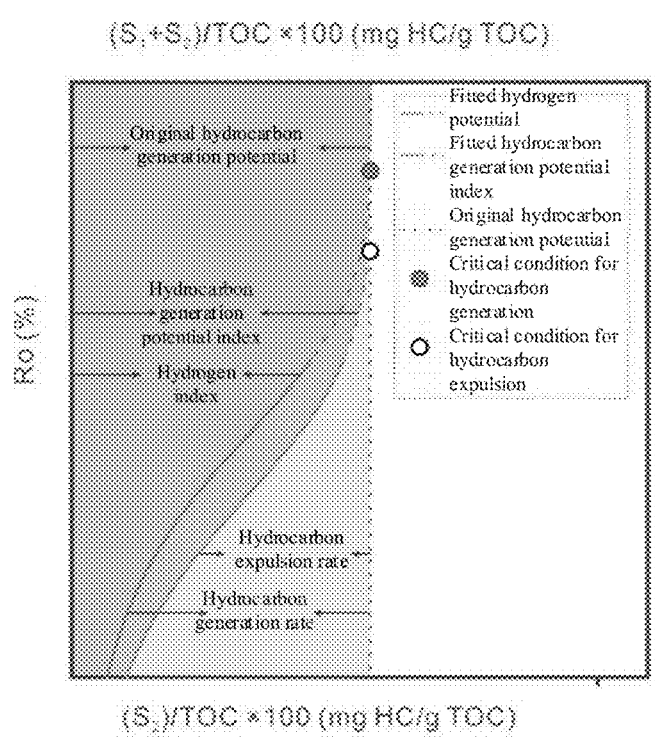
FIG. 2A is the variation of hydrocarbon generation potential of source rocks with thermal evolution.
Figure 2B:
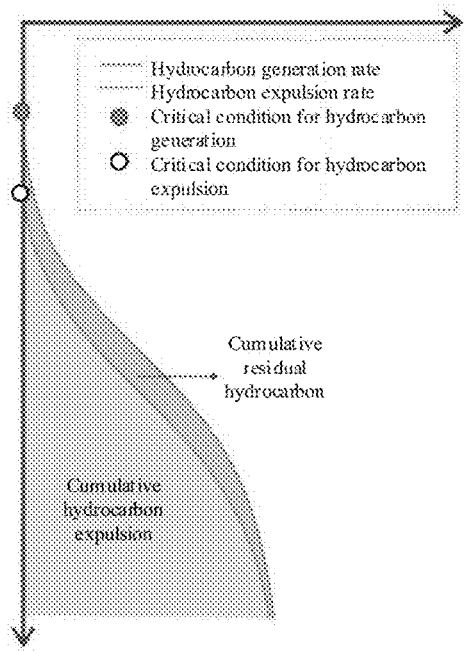
FIG. 2B is the hydrocarbon generation and expulsion rate of source rocks with thermal evolution.

The preferred implementations of the present disclosure are described below with reference to the drawings. Those skilled in the art should understand that the implementations herein are merely intended to explain the technical principles of the present disclosure, rather than to limit the protection scope of the present disclosure.

The present disclosure provides an evaluation method for residual hydrocarbon of post- to over-mature marine source rocks. The method includes the following steps. S100: Establish a hydrocarbon generation potential evolution profile and a hydrogen index evolution profile of post- to over-mature source rocks: obtain a hydrocarbon generation potential index, a hydrogen index and an equivalent vitrinite reflectance through a pyrolysis experiment of the source rocks; and establish a hydrocarbon generation potential evolution profile and a hydrogen index evolution profile of post- to over-mature source rocks for marine strata lacking vitrinite based on the hydrocarbon generation potential index, the hydrogen index and the equivalent vitrinite reflectance, where the hydrocarbon generation potential evolution profile of the source rocks is a diagram showing a relationship between the hydrocarbon generation potential index and the equivalent vitrinite reflectance; and the hydrogen index evolution profile of the source rocks is a diagram showing a relationship between the hydrogen index and the equivalent vitrinite reflectance.

S200: Determine a critical condition for hydrocarbon expulsion of the source rocks, and invert original hydrocarbon generation potential of the source rocks, where the determining a critical condition for hydrocarbon expulsion includes: obtain a homogenization temperature distribution map of fluid inclusions according to an inclusion experiment; determine a main peak value of a homogenization temperature for a first phase of the fluid inclusions based on the homogenization temperature distribution map of the fluid inclusions; and obtain a corresponding minimum $R_{min}$ of an isotherm at the main peak value of the homogenization temperature of the first phase of the inclusions according to a depositional burial history and a thermal evolution history of a typical well, which is $R_{oe}$, meaning a critical maturity for hydrocarbon expulsion corresponding to the critical condition for hydrocarbon expulsion; the inverting original hydrocarbon generation potential of the source rocks includes: obtain a hydrocarbon generation potential index envelope $I_g$ according to the hydrocarbon generation potential evolution profile of the source rocks, $$I_g = \frac{a}{1+e^{-b(R_o-c)}} + d,$$

where a, b, c and d are constants; and obtain original hydrocarbon generation potential of the source rocks based on the hydrocarbon generation potential index envelope and the critical maturity for hydrocarbon expulsion $I_{og}$, $$I_{og} = \frac{a}{1+e^{-b(R_{oe}-c)}} + d.$$

S300: Invert a critical condition for hydrocarbon generation of the source rocks: obtain a hydrogen index envelope HI based on the hydrogen index evolution profile of the source rocks; and obtain a critical condition $R_{og}$ for hydrocarbon generation of the source rocks based on the hydrogen index envelope and the original hydrocarbon generation potential of the source rocks, that is, an equivalent vitrinite reflectance corresponding to an intersection of the hydrogen index envelope and the original hydrocarbon generation potential of the source rocks.

S400: Establish a hydrocarbon generation, expulsion and retention model for the source rocks by means of matrix laboratory (MATLAB) based on the hydrocarbon generation potential evolution profile, the hydrogen index evolution profile, the critical condition for hydrocarbon expulsion, the original hydrocarbon generation potential and the critical condition for hydrocarbon generation of the source rocks.

S500: Determine a hydrocarbon generation rate, a hydrocarbon expulsion rate and a hydrocarbon retention rate of the source rocks: calculate a hydrocarbon generation rate $q_g$, a hydrocarbon expulsion rate $q_e$ and a hydrocarbon retention rate $q_r$ of the source rocks based on the hydrocarbon generation, expulsion and retention model for the source rocks, where $q_g=I_{og}-HI$, $q_e=I_{og}-I_g$, $q_r=q_g-q_e$.

S600: Calculate a hydrocarbon retention intensity and residual hydrocarbon of the source rocks: obtain a hydrocarbon retention intensity $I_r$ of the source rocks in different thermal evolution stages by an integral of the hydrocarbon retention rate, abundance of organic matter and a thickness and of density of the source rocks corresponding to the different thermal evolution stages; and obtain total residual hydrocarbon $Q_r$ in each geological period based on the hydrocarbon retention intensity.

$$I_r = \int_{R_o}^{R_o'} 10^{-3} * q_r * H * \rho * TOC_o * d(R_o).$$

$$TOC_o = TOC * k.$$

$$k = \left(1 - 0.83 * \frac{I_g}{1000}\right) \Big/ \left(1 - 0.83 * \frac{I_{og}}{1000}\right).$$

$$Q_r = \int_{R_o}^{R_o'} 10^{-13} * q_r * H * A * \rho * TOC_o * d(R_o).$$

The present disclosure establishes an evaluation model for residual hydrocarbon of post- to over-mature source rocks without relying on immature to sub-mature samples. The present disclosure provides a scientific basis for the evaluation of shale oil and gas resources, and provides strong theoretical guidance and technical support for the selection and evaluation of shale oil and gas exploration targets.

The present disclosure is described in further detail below with reference to an example of the Sichuan Basin in China.

The Sichuan Basin is located in central China, with an area of about $19 \times 10^4$ km², and it is one of the major natural gas producing areas in China. The Sichuan Basin is a typical superimposed petroliferous basin. After undergoing multi-cycle tectonic movements and the superimposition and transformation of multiple types of basins, the Sichuan Basin has formed multiple sets of source-reservoir-caprock assemblages, which have the characteristics of multi-layered hydrocarbon-bearing. The Ediacaran to Lower Triassic strata in the Sichuan Basin are marine carbonate strata, and the study strata of the present disclosure are in the Upper Ediacaran Dengying Formation. According to lithology and biological characteristics, the Dengying Formation is divided into four lithological members from top to bottom, namely, Deng 4 ($Z_2d^4$), Deng 3 ($Z_2d^3$), Deng 2 ($Z_2d^2$) and Deng 1 ($Z_2d^1$). Algal dolomite, which is widely distributed in the Sichuan Basin, is an important Ediacaran source rock in the Sichuan Basin. It is mainly distributed in the Deng 4 ($Z_2d^4$) and Deng 2 ($Z_2d^2$) members. This type of source rock has a buried depth of more than 5,000 m, and has reached the post- to over-mature thermal evolution stage, with a thickness of 300-1,350 m.

Referring to FIGS. 1 to 7, the present disclosure provides an evaluation method for residual hydrocarbon of post- to over-mature marine source rocks. The method established a conceptual model for hydrocarbon expulsion of post- to over-mature source rocks, as shown in FIGS. 2A and 2B, and was implemented by the following steps. S100: A hydrocarbon generation potential evolution profile and a hydrogen index evolution profile of post- to over-mature source rocks were established. According to parameters obtained from a pyrolysis experiment of the Ediacaran algal dolomite source rocks in the Sichuan Basin, a hydrocarbon generation potential index ($100 \times (S_1+S_2)/TOC$), a hydrogen index ($100 \times S_2/TOC$) and an equivalent vitrinite reflectance $R_o$ were calculated.

Figure 3:
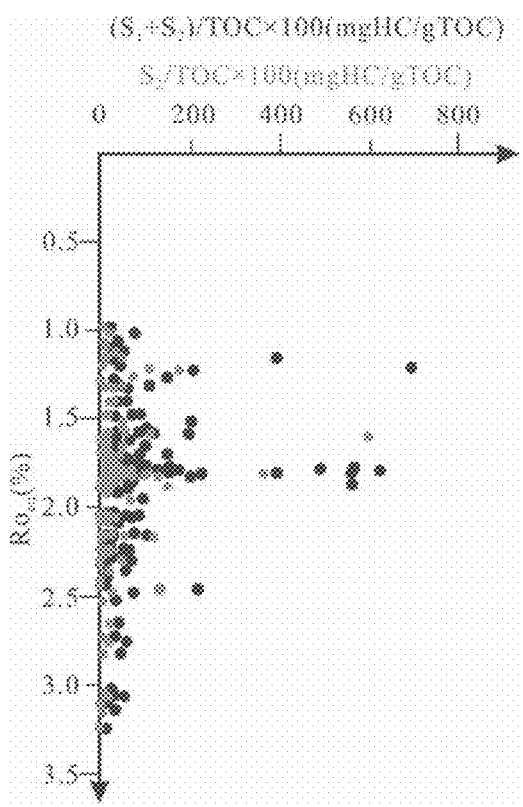
FIG. 3 is a hydrocarbon generation potential and hydrogen index evolution profile of post- to over-mature Ediacaran algal dolomite source rocks in the Sichuan Basin, China.

A hydrocarbon generation potential evolution profile and a hydrogen index evolution profile of post- to over-mature source rocks were established for marine strata lacking vitrinite, as shown in FIG. 3, based on the hydrocarbon generation potential index, the hydrogen index and the equivalent vitrinite reflectance. The hydrocarbon generation potential evolution profile of the source rocks shows a change of the hydrocarbon generation potential index with the equivalent vitrinite reflectance, and the hydrogen index evolution profile of the rocks shows a change of the hydrogen index with the equivalent vitrinite reflectance.

Further, $R_0=0.0078T_{max}-1.3654$, where $T_{max}$ is a peak temperature in the pyrolysis experiment of the source rocks; and $R_0$ is in %, and $T_{max}$ is in °C.

Figure 4:
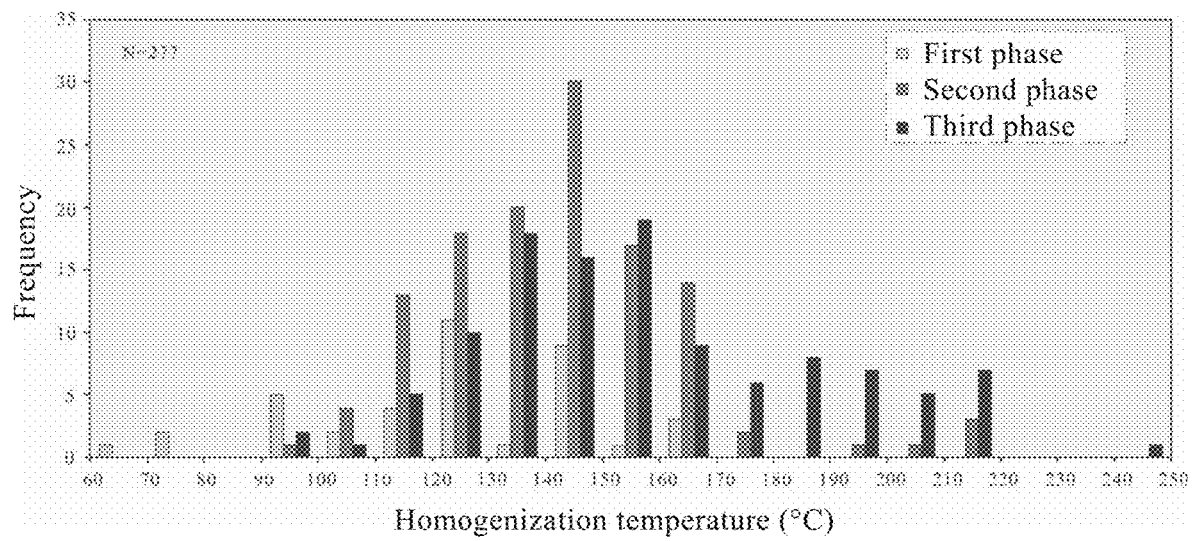
FIG. 4 is a homogenization temperature distribution map of Ediacaran dolomite fluid inclusions in the Sichuan Basin.
Figure 5:
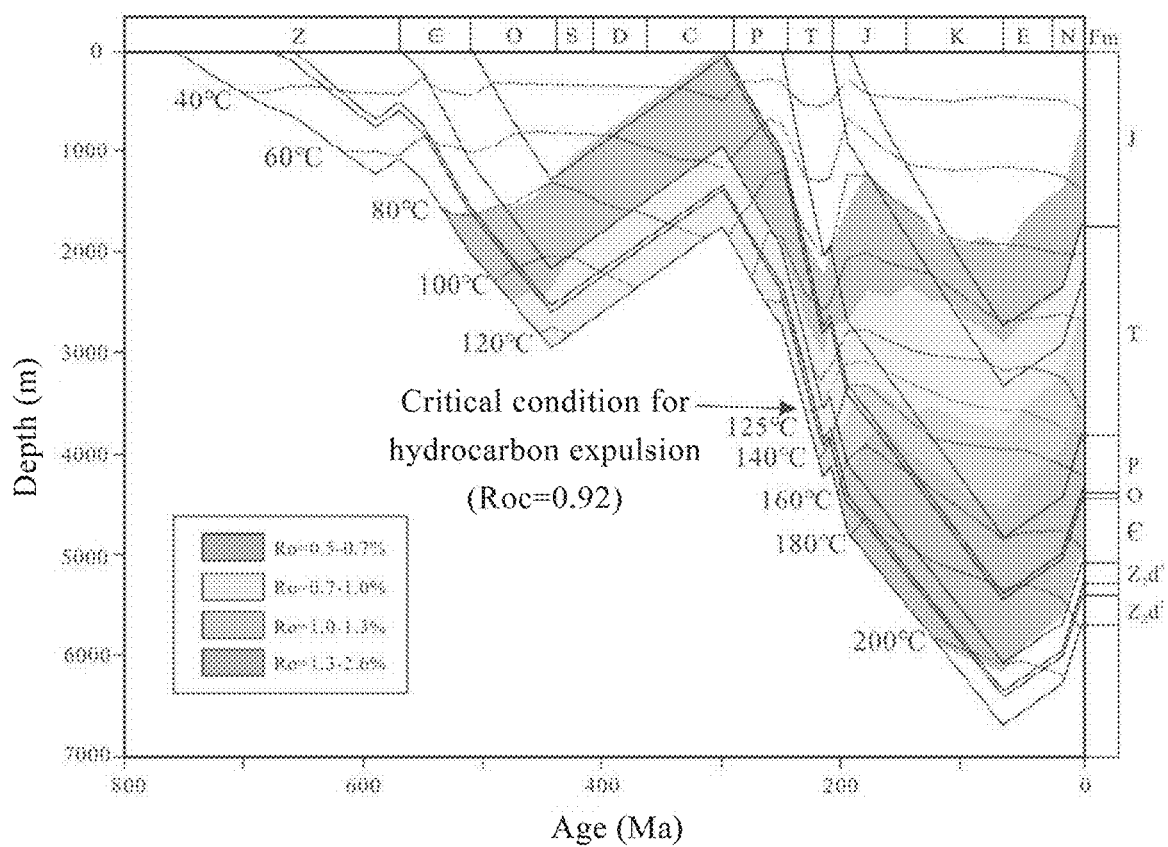
FIG. 5 is a depositional burial history and thermal evolution history of Well Moxi 8 in the Sichuan Basin.

S200: A critical condition for hydrocarbon expulsion from the Ediacaran algal dolomite source rocks in the Sichuan Basin was determined, and original hydrocarbon generation potential of the source rocks was inverted. Through microscopic thin section analysis and geological analysis, three phases of inclusions were found in the Dengying Formation in the Sichuan Basin. The first phase of inclusions was formed in dolomite grains. Through experimental analysis of the inclusions in the Dengying Formation, a homogenization temperature distribution map of the fluid inclusions was obtained, as shown in FIG. 4. A main peak value of the homogenization temperature of the first phase of inclusions was determined as 120-130° C. For quantitative characterization, 125° C. was taken as the final main peak value of the homogenization temperature, which meant that the source rocks began to expel a large amount of hydrocarbons at this paleo-geothermic temperature. According to a depositional burial history and a thermal evolution history of the typical Well Moxi 8 in the Sichuan Basin (FIG. 5), a critical maturity $R_{oe}$ for hydrocarbon expulsion of the algal dolomite source rocks in the Dengying Formation was inverted. A minimum $R_0$ on the 125° C. isotherm of the Dengying Formation was the critical maturity $R_{oe}$ for hydrocarbon expulsion from the algal dolomite source rocks of the Dengying Formation. $R_{oe}$ was taken as 0.92%, which meant that the Ediacaran algal dolomite source rocks in the Sichuan Basin began to expel a large amount of hydrocarbons when $R_0$ reached 0.92%, that is, the critical maturity for hydrocarbon expulsion ($R_{oe}$) was correspondingly $R_{oe}=0.92\%$.

A hydrocarbon generation potential index envelope $I_g$ was obtained according to the hydrocarbon generation potential evolution profile of the source rocks, $$I_g = \frac{702.64}{1 + e^{-2.17(R_o+3.55)}} + 53.48.$$

An original hydrocarbon generation potential $I_{og}$ of the source rocks was obtained based on the hydrocarbon generation potential index envelope and the critical maturity for hydrocarbon expulsion. Specifically, a mathematical relationship between the hydrocarbon generation potential index envelope and the degree of thermal evolution was fitted. A hydrocarbon generation potential corresponding to the critical maturity for hydrocarbon expulsion on the hydrocarbon expulsion evolution profile of the source rocks was the original hydrocarbon generation potential of the source rocks. The original hydrocarbon generation potential of the Ediacaran source rocks in the Sichuan Basin was calculated as $I_{og}=756$ mg·HC/g TOC.

Further, a critical condition for hydrocarbon generation in the Ediacaran algal dolomite source rocks in the Sichuan Basin was inverted.

A hydrogen index envelope HI was obtained based on the established hydrogen index evolution profile of the Ediacaran algal dolomite source rocks in the Sichuan Basin, $$HI = \frac{722.41}{1 + e^{-1.95(R_o+3.52)}} + 33.83.$$

According to the obtained original hydrocarbon generation potential and hydrogen index envelope of the Ediacaran algal dolomite source rocks in the Sichuan Basin, the critical condition for hydrocarbon generation in the source rocks was obtained, that is, an equivalent vitrinite reflectance corresponding to an intersection of the hydrogen index envelope and the original hydrocarbon generation potential of the source rocks. In this example, $R_{og}=0.51\%$.

Figure 6:
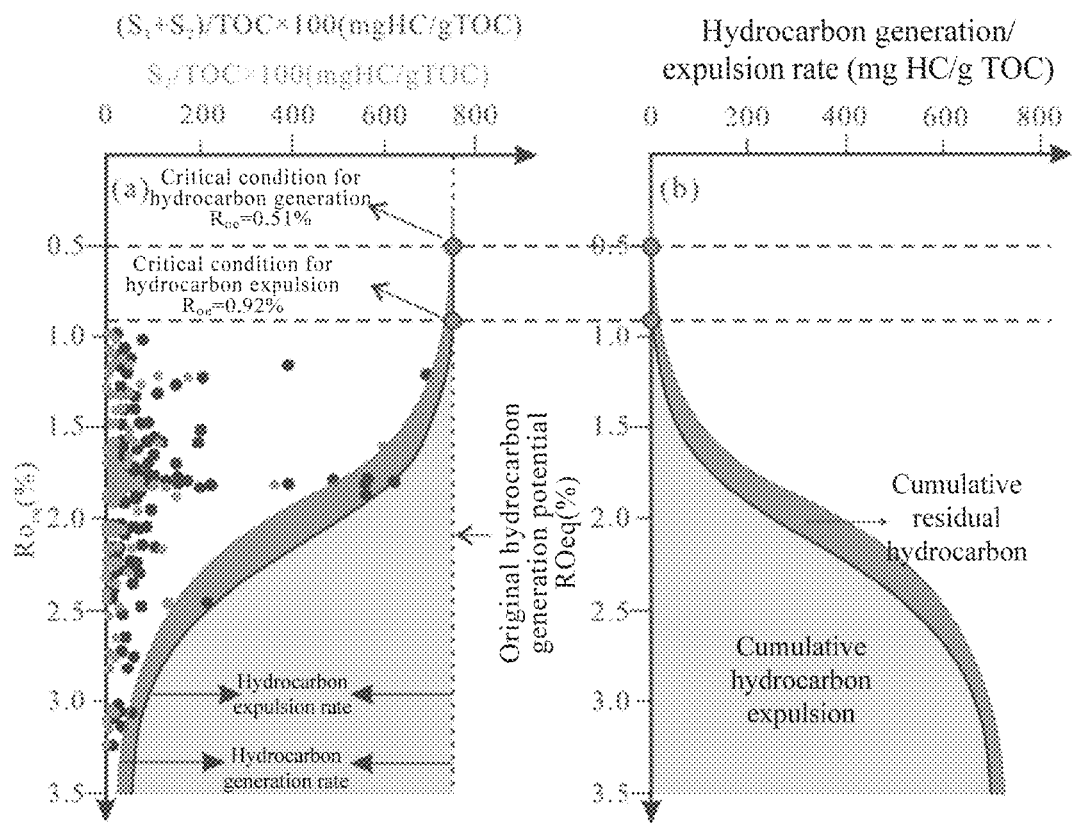
FIG. 6 is a hydrocarbon generation, expulsion and retention model for the post- to over-mature Ediacaran algal dolomite source rocks in the Sichuan Basin.

S400: A hydrocarbon generation, expulsion and retention model for the source rocks was established by means of matrix laboratory (MATLAB) based on the hydrocarbon generation potential evolution profile, the hydrogen index evolution profile, the critical condition for hydrocarbon expulsion, the original hydrocarbon generation potential and the critical condition for hydrocarbon generation. In this example, a hydrocarbon generation, expulsion and retention model for the Ediacaran algal dolomite source rocks in the Sichuan Basin was established, as shown in FIG. 6, and $R_{og}$, $R_{oe}$, HI, $I_g$ and $I_{og}$ were marked in the model. In this model, the hydrocarbon generation potential and hydrogen index of the source rocks decreased with the increase of thermal maturity.

S500: A hydrocarbon generation rate, a hydrocarbon expulsion rate and a hydrocarbon retention rate of the Ediacaran algal dolomite source rocks in the Sichuan Basin were determined. A hydrocarbon generation rate $q_g$, a hydrocarbon expulsion rate $q_e$ and a hydrocarbon retention rate $q_r$ of the source rocks were calculated based on the hydrocarbon generation, expulsion and retention model for the source rocks.

$$q_g = I_{og} - HI = 722.17 - \frac{722.41}{1 + e^{-1.95(R_o+3.52)}}.$$

$$q_e = I_{og} - I_g = 702.52 - \frac{702.64}{1 + e^{-2.17(R_o+3.55)}}.$$

$$q_r = q_g - q_e = 19.65 + \frac{702.64}{1 + e^{-2.17(R_o+3.55)}} - \frac{722.41}{1 + e^{-1.95(R_o+3.52)}}.$$

S600: A hydrocarbon retention intensity and residual hydrocarbon of the Ediacaran algal dolomite source rocks in the Sichuan Basin were determined. A hydrocarbon retention intensity $I_r$ of the source rocks in different thermal evolution stages was calculated by an integral of the hydrocarbon retention rate, abundance of organic matter and a thickness and density of the source rocks corresponding to the different thermal evolution stages, and total residual hydrocarbon $Q_r$ in each geological period was calculated based on the hydrocarbon retention intensity.

$$I_r = \int_{R_o}^{R_o'} 10^{-3} * q_r * H * \rho * TOC_O * d(R_o),$$

where H was the thickness of the source rocks; ρ was the density of the source rocks; A was a distribution area of the source rocks; and $TOC_O$ was original TOC of the source rock.

$$TOC_o = TOC * k.$$

$$k = \left(1 - 0.83 * \frac{I_g}{1000}\right)\left(1 - 0.83 * \frac{I_{og}}{1000}\right).$$

$$Q_r = \int_{R_o}^{R_o'} 10^{-13} * q_r * H * A * \rho * TOC_O * d(R_o).$$

Figure 7:
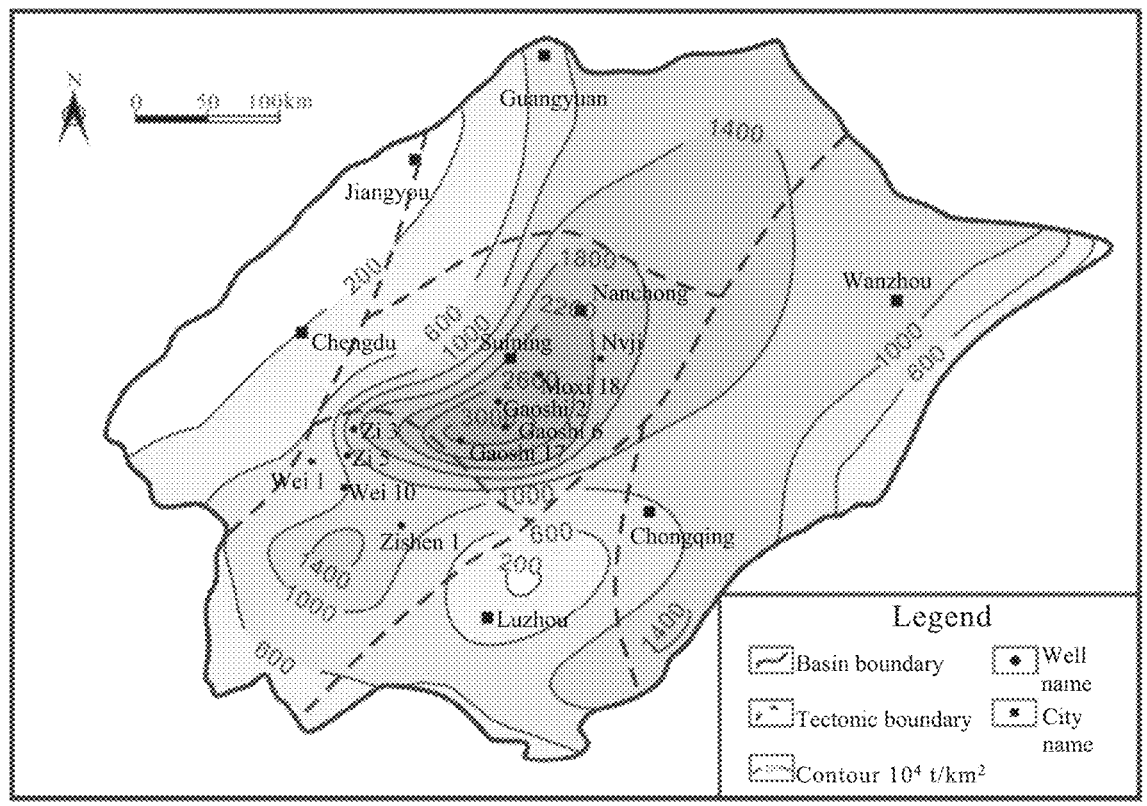
FIG. 7 is a current hydrocarbon retention intensity map of the Ediacaran algal dolomite source rocks in the Sichuan Basin.

Further, refer to FIG. 7, FIG. 7 is a current hydrocarbon retention intensity map of the Ediacaran algal dolomite source rocks in the Sichuan Basin. A maximum hydrocarbon retention intensity $I_r$ reached $3200 \times 10^4$ t/km$^2$, and the total residual carbon $Q_r$ of the Ediacaran algal dolomite source rocks in the Sichuan Basin was $1.66 \times 10^{12}$ t toe. An area with the highest hydrocarbon retention intensity was determined as a favorable exploration target.

The above examples are merely intended to illustrate the present disclosure, and the implementation steps of the method can be changed. Any equivalent changes and improvements made on the basis of the technical solutions of the present disclosure should not be excluded from the protection scope of the present disclosure.

Although the present disclosure has been described with reference to the preferred examples, various improvements can be made and components therein can be replaced with equivalents without departing from the scope of the present disclosure. In particular, as long as there is no structural conflict, the technical features in the examples can be combined in any way. The present disclosure is not limited to the specific examples disclosed herein, but shall include all technical solutions falling within the scope of the claims.

In the description of the present disclosure, terms such as "central", "upper", "lower", "left", "right", "vertical", "horizontal", "inner", and "outer" indicate orientation or position relationships based on the drawings. They are merely intended to facilitate description, rather than to indicate or imply that the mentioned apparatus or components must have the specific orientation and must be constructed and operated in the specific orientation. Therefore, these terms should not be construed as a limitation to the present disclosure. Moreover, the terms such as "first", "second", and "third" are used only for description and are not intended to indicate or imply relative importance.

It should be noted that in the description of the present disclosure, unless otherwise clearly specified, meanings of terms "install", "connect with" and "connect to" should be understood in a broad sense. For example, the connection may be a fixed connection, a removable connection, or an integral connection; may be a mechanical connection or an electrical connection; may be a direct connection or an indirect connection via a medium; or may be an internal connection between two assemblies. Those skilled in the art should understand the specific meanings of the above terms in the present disclosure based on specific situations.

In addition, terms "include", "comprise", or any other variations thereof are intended to cover non-exclusive inclusions, so that a process, an article, or a device/apparatus including a series of elements not only includes those elements, but also includes other elements that are not explicitly listed, or also includes inherent elements of the process, the article or the device/apparatus.

The technical solutions of the present disclosure are described with reference to the preferred implementations and drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions derived by making these changes or substitutions should fall within the protection scope of the present disclosure.

What is claimed is:

1. An evaluation method for residual hydrocarbon of post- to over-mature marine source rocks comprising steps of:
   A) collecting samples of post- to over-mature marine source rocks to be evaluated from a formation;
   B) establishing a hydrocarbon generation potential evolution profile and a hydrogen index evolution profile of the post- to over-mature source rocks comprising steps of:
      obtaining a hydrocarbon generation potential index, a hydrogen index and an equivalent vitrinite reflectance through a pyrolysis experiment of the collected samples of post- to over-mature source rocks; and
      establishing the hydrocarbon generation potential evolution profile and the hydrogen index evolution profile of post- to over-mature post- to over-mature source rocks in marine strata lacking vitrinite based on the hydrocarbon generation potential index, the hydrogen index and the equivalent vitrinite reflectance, wherein
      the hydrocarbon generation potential evolution profile of the post- to over-mature source rocks is a diagram showing a relationship between the hydrocarbon generation potential index and the equivalent vitrinite reflectance; and the hydrogen index evolution profile of the post- to over-mature source rocks is a diagram showing a relationship between the hydrogen index and the equivalent vitrinite reflectance;
      the hydrocarbon generation potential index is $100 \times (S_1 + S_2)/TOC$, wherein $S_1$, $S_2$ are hydrocarbon yields per unit mass of source rock samples heated to 300° C. and 300-600°

C. respectively, mg·HC/g; TOC is total organic carbon (TOC) per unit mass of the post- to over-mature source rocks, mg/g;

the hydrogen index is $100 \times S_2/TOC$; and the equivalent vitrinite reflectance is $R_o$, $R_0 = 0.0078 T_{max} - 1.3654$, wherein $T_{max}$ is a maximum peak pyrolysis temperature in the pyrolysis experiment of the post- to over-mature source rocks;

C) determining a critical condition for hydrocarbon expulsion of the post- to over-mature source rocks, and inverting original hydrocarbon generation potential of the post- to over-mature source rocks comprising steps of:

obtaining a homogenization temperature distribution map of fluid inclusions according to an inclusion experiment;

determining a main peak value of a homogenization temperature for a first phase of the fluid inclusions based on the homogenization temperature distribution map of the fluid inclusions; and obtaining a corresponding minimum $R_{min}$ of an isotherm at the main peak value of the homogenization temperature of the first phase of the fluid inclusions according to a depositional burial history and a thermal evolution history of a typical well, wherein the corresponding minimum $R_{min}$ is $R_{oe}$, and $R_{oe}$ is a critical maturity for the hydrocarbon expulsion corresponding to the critical condition for the hydrocarbon expulsion; and wherein inverting the original hydrocarbon generation potential of the post- to over-mature source rocks comprises:

obtaining a hydrocarbon generation potential index envelope $I_g$ according to the hydrocarbon generation potential evolution profile of the post- to over-mature source rocks by the following equation, $$I_g = \frac{a}{1 + e^{-b(R_o - c)}} + d,$$

wherein a, b, c and d are constants; and obtaining the original hydrocarbon generation potential $I_{og}$ of the post- to over-mature source rocks based on the hydrocarbon generation potential index envelope and the critical maturity for hydrocarbon expulsion by the following equation, $$I_{og} = \frac{a}{1 + e^{-b(R_{oe} - c)}} + d;$$

D) inverting a critical condition for hydrocarbon generation of the post- to over-mature source rocks, wherein a method of inverting the critical condition for the hydrocarbon generation of the post- to over-mature source rocks comprises:

obtaining a hydrogen index envelope HI based on the hydrogen index evolution profile of the post- to over-mature source rocks by the following equation, $$HI = \frac{e}{1 + e^{-f(R_o - g)}} + h,$$

wherein e, f, g and h are constants; and obtaining the critical condition $R_{og}$ for the hydrocarbon generation of the post- to over-mature source rocks based on the hydrogen index envelope and the original hydrocarbon generation potential of the post- to over-mature source rocks, wherein $R_{og}$ is an equivalent vitrinite reflectance corresponding to an intersection of the hydrogen index envelope and the original hydrocarbon generation potential of the post- to over-mature source rocks;

E) establishing a hydrocarbon generation, expulsion and retention model for the post- to over-mature source rocks comprising the steps of:

establishing the hydrocarbon generation, expulsion and retention model for the post to over-mature source rocks by means of matrix laboratory (MATLAB) based on the hydrocarbon generation potential evolution profile of the post- to over-mature source rocks, the hydrogen index evolution profile of the post- to over-mature source rocks, the critical condition for hydrocarbon expulsion of the post- to over-mature source rocks, the original hydrocarbon generation potential of the post- to over-mature source rocks and the critical condition for hydrocarbon generation of the post- to over-mature source rocks; and marking $R_{og}$, $R_{oe}$, HI, $I_g$ and $I_{og}$ in the hydrocarbon generation, expulsion and retention model;

F) calculating a hydrocarbon generation rate, a hydrocarbon expulsion rate and a hydrocarbon retention rate of the post- to over-mature source rocks based on the hydrocarbon generation, expulsion and retention model for the post- to over-mature source rocks, wherein the hydrocarbon generation rate of the post- to over-mature source rocks is $q_g$, $q_g = I_{og} - HI$; the hydrocarbon expulsion rate of the post- to over-mature source rocks is $q_e$, $q_e = I_{og} - I_g$; and the hydrocarbon retention rate of the post- to over-mature source rocks is $q_r$, $q_r = q_g - q_e$; and G) calculating a hydrocarbon retention intensity and residual hydrocarbon of the post to over-mature source rocks comprising the steps of:

obtaining the hydrocarbon retention intensity $I_r$ of the post- to over-mature source rocks in different thermal evolution stages by an integral of the hydrocarbon retention rate, abundance of organic matter and a thickness and density of the post- to over-mature source rocks corresponding to the different thermal evolution stages by the following equation, $$I_r = \int_{R_o}^{R_o} 10^{-3} * q_r * H * \rho * TOC_O * d(R_o),$$

wherein H is the thickness of the post- to over-mature source rocks; $\rho$ is the density of the post- to over-mature source rocks; A is a distribution area of the post- to over-mature source rocks; and $TOC_O$ is original TOC of the post- to over-mature source rocks; and obtaining total residual hydrocarbon $Q_r$ in each geological period based on the hydrocarbon retention intensity, wherein $$Q_r = \int_{R_o}^{R_o} 10^{-13} * q_r * H * A * \rho * TOC_O * d(R_o), \text{ and}$$

H) exploring an area of the formation with the highest hydrocarbon retention intensity $I_r$ and total residual carbon $Q_r$.

2. The evaluation method for residual hydrocarbon of post- to over-mature marine source rocks according to claim 1, wherein $TOC_o = TOC * k$; and $$k = \left(1 - 0.83 * \frac{I_g}{1000}\right) \Big/ \left(1 - 0.83 * \frac{I_{og}}{1000}\right).$$

\* \* \* \* \*